United States Patent
Metzger et al.

(10) Patent No.: US 7,025,788 B2
(45) Date of Patent: Apr. 11, 2006

(54) KNEE JOINT PROSTHESIS

(75) Inventors: Robert G. Metzger, Wakarusa, IN (US); Jacy C. Hoeppner, Syracuse, IN (US)

(73) Assignee: Biomet, Inc., Warsaw, IN (US)

( * ) Notice: Subject to any disclaimer, the term of this patent is extended or adjusted under 35 U.S.C. 154(b) by 163 days.

(21) Appl. No.: 10/289,585

(22) Filed: Nov. 7, 2002

(65) Prior Publication Data

US 2003/0055508 A1  Mar. 20, 2003

Related U.S. Application Data

(63) Continuation-in-part of application No. 09/792,172, filed on Feb. 23, 2001, now abandoned.

(51) Int. Cl.
*A61F 2/38* (2006.01)

(52) U.S. Cl. ............... 623/20.15; 623/20.34; 623/23.46

(58) Field of Classification Search ............ 623/20.15, 623/20.32, 20.34, 20.35, 20.36, 23.18, 23.44, 623/23.45, 23.46
See application file for complete search history.

(56) References Cited

U.S. PATENT DOCUMENTS

| | | | |
|---|---|---|---|
| 4,676,797 A | 6/1987 | Anapliotis et al. ............ 623/18 |
| 4,950,297 A | 8/1990 | Elloy et al. ................... 623/20 |
| 5,609,642 A | 3/1997 | Johnson et al. ............... 623/20 |
| 5,776,200 A | 7/1998 | Johnson et al. ............... 623/20 |
| 5,782,920 A | 7/1998 | Colleran .................. 623/20.15 |
| 5,782,921 A | 7/1998 | Colleran .................. 623/20.15 |
| 6,063,091 A | 5/2000 | Lombardo et al. ............ 606/88 |
| 6,146,424 A | 11/2000 | Gray, Jr. et al. ......... 623/20.34 |
| 6,149,687 A | 11/2000 | Gray, Jr. et al. ......... 623/20.34 |
| 6,162,255 A | 12/2000 | Oyola ..................... 623/20.34 |
| 6,171,342 B1 | 1/2001 | O'Neil .................... 623/20.15 |
| 6,214,052 B1 | 4/2001 | Burkinshaw ............. 623/20.34 |
| 6,217,619 B1 | 4/2001 | Keller ..................... 623/20.15 |
| 6,228,091 B1 | 5/2001 | Lombardo et al. ............ 606/88 |
| 6,306,172 B1 | 10/2001 | O'Neil .................... 623/20.15 |
| 6,712,858 B1 * | 3/2004 | Grundei et al. .......... 623/23.45 |
| 6,755,864 B1 * | 6/2004 | Brack et al. ............. 623/20.29 |
| 2003/0074078 A1 * | 4/2003 | Doubler et al. .......... 623/22.42 |
| 2003/0204263 A1 * | 10/2003 | Justin et al. ............. 623/20.15 |

* cited by examiner

*Primary Examiner*—David H. Willse
*Assistant Examiner*—Javier G. Blanco
(74) *Attorney, Agent, or Firm*—Harness, Dickey & Pierce, P.L.C.

(57) ABSTRACT

A modular tibial component for a knee joint prosthesis. The modular tibial component includes a tray, a stem and an adapter assembly. The tray includes a support surface and downwardly extending extension having a generally circular shape. The stem includes a main body portion and an upwardly extending extension. The adapter assembly connects the tray and the stem. The adapter assembly includes a first generally cylindrical cavity receiving the downwardly extending extension of the tray and a second generally cylindrical cavity receiving the upwardly extension of the stem.

8 Claims, 9 Drawing Sheets

KNEE JOINT PROSTHESIS

CROSS-REFERENCE TO RELATED APPLICATIONS

This is a continuation-in-part application of U.S. Ser. No. 09/792,172, filed Feb. 23, 2001, now abandoned.

FIELD OF THE INVENTION

The present invention relates generally to a joint prosthesis and more particularly to a knee joint prosthesis having a modular tibial component with an offset tibial stem.

BACKGROUND OF THE INVENTION

A knee joint prosthesis typically comprises a femoral component and a tibial component. The femoral component and tibial component are designed to be surgically attached to the distal end of the femur and the proximal end of the tibia respectively. The femoral component is further designed to cooperate with the tibial component in simulating the articulating motion of an anatomical knee joint. Knee joint prostheses, in combination with ligaments and muscles, attempt to duplicate natural knee motion as well as absorb and control forces generated during the range of flexion.

While known knee joint prostheses have proven to be effective in replacing the anatomical knee joint, they nevertheless have several disadvantages. For example, knee joint prostheses sometimes lack interchangeability between a femoral component designed specifically for a right knee or a left knee and a particular component. In this regard, in a normally shaped tibia, the central canal is typically offset from the center of the tibial articulating surfaces or the center of the tibial plateau. The stems of most prior tibial implants have been positioned centrally to the implant base or tibial tray. Although a central location of the stem allows for particular implant to be used for either the right or left knee, such a stem position is associated with drawbacks. The primary drawback is that the centrally located stem was substantially offset from the center of the tibial canal itself when the base of the implant was aligned with the resected tibial surface.

To a more limited extent, it is also known to provide a knee joint prosthesis with an offset tibia stem. While knee joint prosthesis with offset tibial stems provide certain identified advantages, they nevertheless can be the subject of certain improvement.

SUMMARY OF THE INVENTION

According to one aspect of the present invention, the invention relates to a tibial component for a knee joint prosthesis having an offset stem.

One particular advantage of the present invention is to provide a tibial component of a knee joint prosthesis having a common tibial tray and a plurality of tibial stems with various offsets for selectively engaging the tibial tray.

Another advantage of the present invention is to provide a tibial component of a knee joint prosthesis having a offset modular stem that securely engages a tibial tray.

Another advantage of the present invention is to provide a modular component of a knee joint prosthesis that permits different degrees of stem offset with minimal inventory.

Another advantage of the present invention is the provision of a tibial component of a knee joint prosthesis having a stem which is offset immediately below a tibial tray.

Another advantage of the present invention is the provision of a modular tibial component of a knee joint prosthesis having a stem that easily and securely engages a tray.

Another advantage of the present invention is the provision of a modular tibial component of a knee joint prosthesis which provides an offset in any direction within the transverse plane.

In one form, the present invention provides a modular tibial component for a knee joint prosthesis. The modular tibial component includes a tray, a stem and an adapter assembly. The tray includes a support surface and downwardly extending extension having a generally circular shape. The stem includes a main body portion and an upwardly extending extension. The adapter assembly connects the tray and the stem. The adapter assembly includes a first generally cylindrical cavity receiving the downwardly extending extension of the tray and a second generally cylindrical cavity receiving the upwardly extending extension of the stem.

Additional advantages and features of the present invention will become apparent from the following description and appended claims, taken in conjunction with the accompanying drawings.

BRIEF DESCRIPTION OF THE DRAWINGS

The present invention will become more fully understood from the detailed description and the accompanying drawings, wherein:

FIGS. 21A–21C are top, side and bottom views, respectively, of the locking element of the knee joint prosthesis of FIG. 19.

DETAILED DESCRIPTION OF THE PREFERRED EMBODIMENTS

Figure 1:
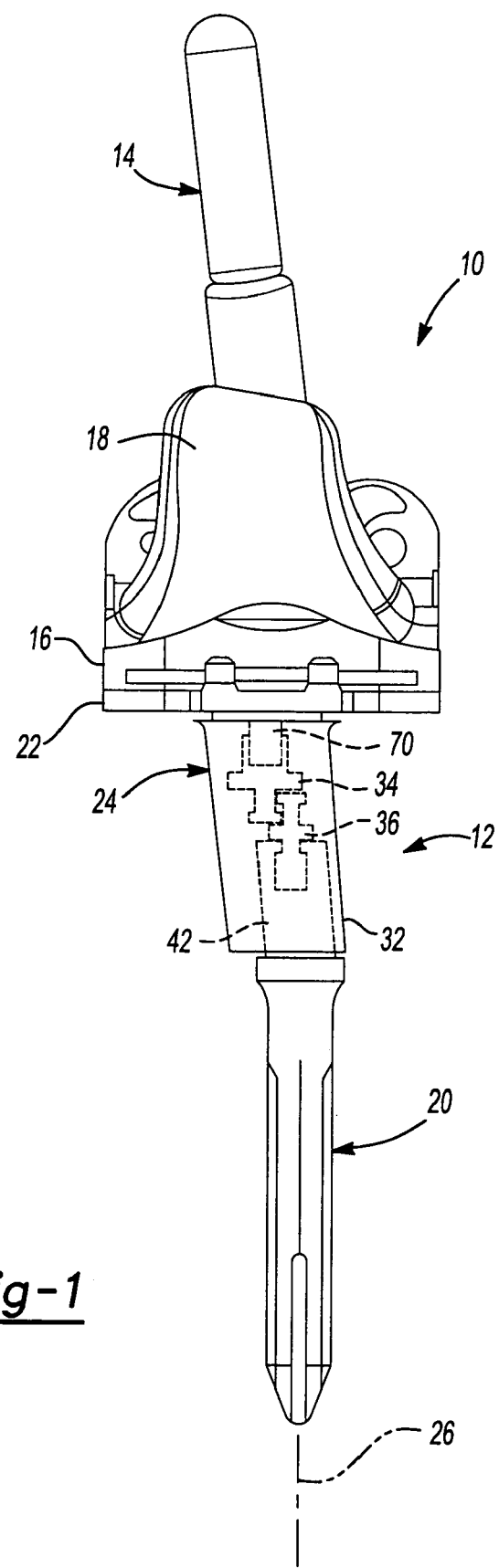
FIG. 1 is a front view illustration of a knee joint prosthesis, the knee joint prosthesis illustrated to include a first adapter assembly for providing a first predetermined offset according to the teachings of a preferred embodiment of the present invention.

With initial reference to FIG. 1, a knee joint prosthesis constructed in accordance with the teachings of a preferred embodiment of the present invention is illustrated and generally identified at reference number 10. The knee joint prosthesis 10 is generally shown to include a tibial component 12 and a femoral component 14. The tibial component 12 supports a bearing 16 which engages an articulation surface 18 of the femoral component 14. Insofar as the present invention is concerned, it will be understood that the femoral component 14 and the bearing 16 shown in FIG. 1 are conventional in construction.

The tibial component 12 illustrated in FIG. 1 will be understood to be modular in construction and generally include a stem 20, a tray 22, and a first adapter assembly 24. In a manner which will be discussed more fully below, the adapter assembly 24 connects the tray 22 and the stem 20 so as to provide an offset to the stem 20 in the transverse plane. Explaining further, when the stem 20 is attached to the tray 22 through the first adapter assembly 24, a central axis of the stem 20 is offset from a central axis 27 of a downwardly extending extension 30 of the tray 22. In the embodiment illustrated, the first adapter assembly 24 provides a first offset of approximately 5 mm. It will become apparent below that the offset can be in any direction in the transverse plane.

Figure 2:
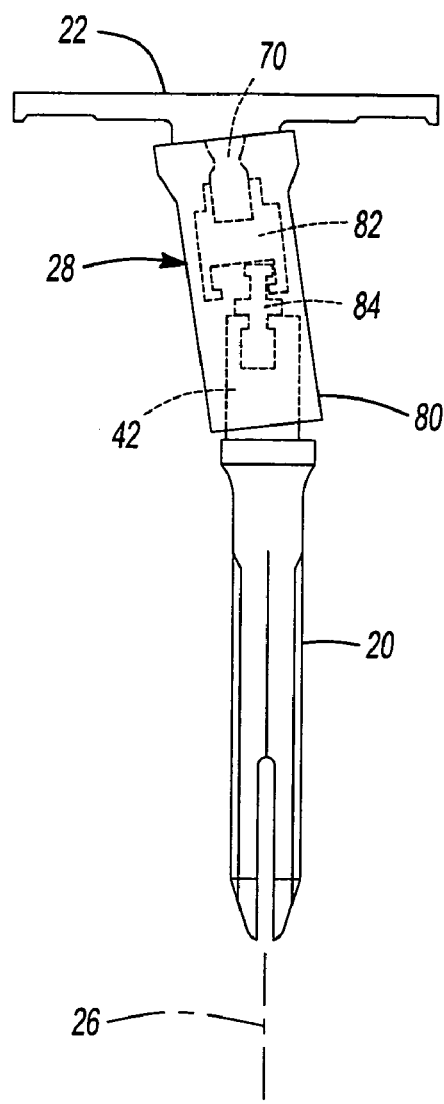
FIG. 2 is front view of a modular tibial component for a knee joint prosthesis including a second adapter assembly according to the teachings of the present invention for providing a second predetermined offset.
Figure 3:
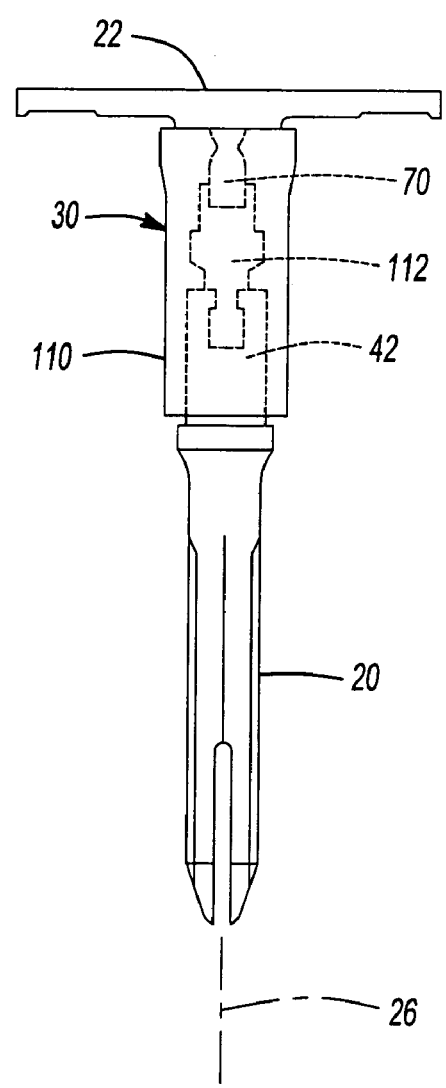
FIG. 3 is front view of a modular tibial component for a knee joint prosthesis including a third adapter assembly according to the teachings of the present invention which does not include an offset.
Figure 4:
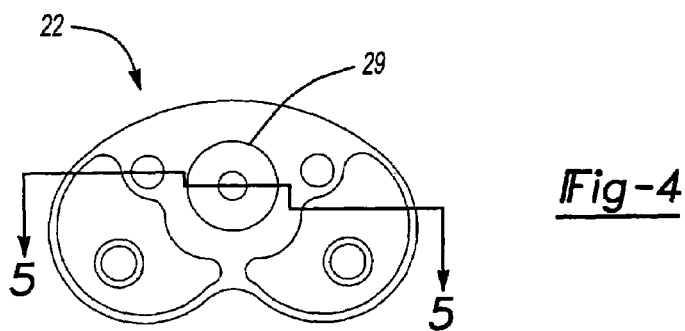
FIG. 4 is a bottom view of the tibial tray of the knee joint prosthesis of FIG. 1.
Figure 5:
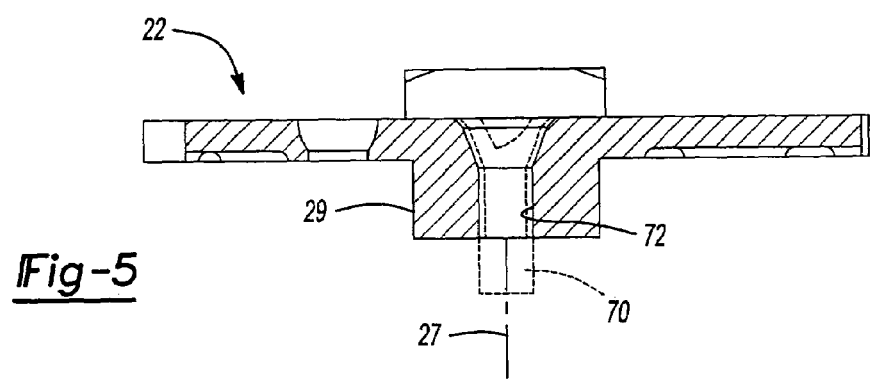
FIG. 5 is a cross-sectional view taken along the line 5—5 of FIG. 4.
Figure 6:
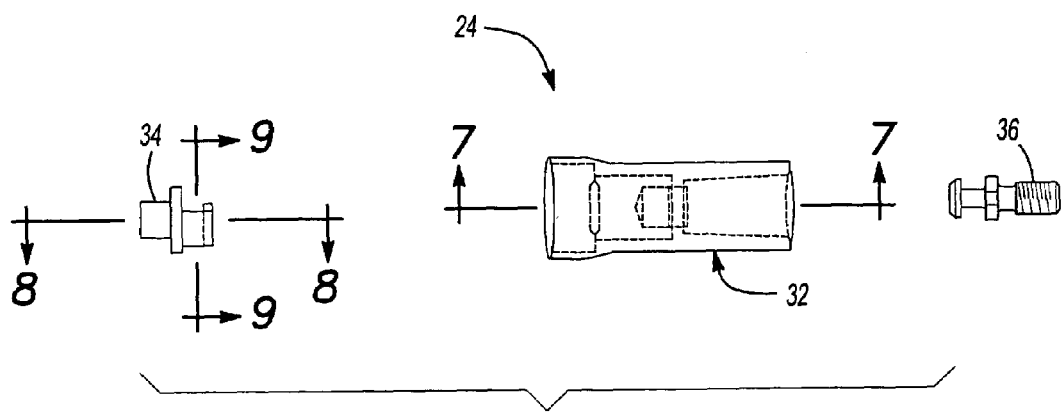
FIG. 6 is an exploded view of a portion of the modular tibial component of FIG. 1.
Figure 7:
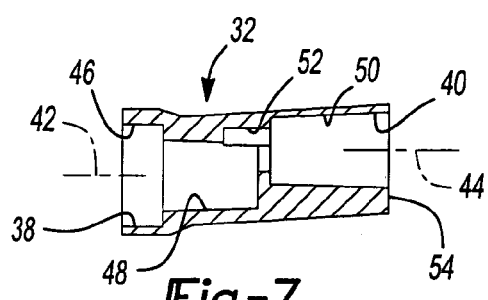
FIG. 7 is a cross-sectional view taken along the line 7—7 of FIG. 6.

With brief reference to FIGS. 2 and 3, second and third adapter assemblies 28 and 30 according to the teachings of the preferred embodiment of the present invention are illustrated, respectively. The second and third adapter assemblies 28 and 30 are shown connecting the tray 22 and stem 20 of FIG. 1. As will be discussed more fully below, the second adapter assembly 28 provides a second offset which in the embodiment illustrated is approximately 2.5 mm. The third adapter assembly is a neutral adapter assembly 30 and does not provide any offset. Explaining further, the central axis 26 of the stem 20 is aligned with the central axis 27 of the downwardly extending extension 29 of the tray 22. It will be appreciated by those skilled in the art that the particular degrees of offset provided by the various adapter assemblies 24, 28, and 30 of the present invention are strictly a matter of design choice. Alternate offsets will be understood to fall within the scope of the present invention.

With continued reference to FIG. 1 and additional reference to FIGS. 4 through 10, the first adapter assembly 24 will be further described. The first adapter assembly 24 is illustrated to generally include an adapter body 32, a locking insert member 34 and a stem insert member 36. The adapter body 32 of the first adapter assembly 24 is shown to include a first generally cylindrical cavity 38 for receiving the downwardly extending extension 29 of the tray 22 and a second generally cylindrical cavity 40 for receiving and upwardly extending extension 42 of the stem 20. The first generally cylindrical cavity 38 includes a first central axis 42 and the second generally cylindrical cavity 40 includes a second generally cylindrical axis 44. In the embodiment illustrated, the first central axis 42 and the second central axis 44 are parallel to one another and spaced apart. Insofar as the first adapter assembly 24 provides a 5 mm offset, the first and second central axes 42 and 44 are spaced apart 5 mm.

The first generally cylindrical cavity 38 includes a first portion 46 for directly receiving the downwardly extending extension 29 of the tray 22 and a second reduced diameter portion 48 which receives the locking insert 34. The first portion 46 preferably tapers slightly as it extends into the adapter body 32 from a top end of the adapter body 32. The second generally cylindrical cavity 40 similarly includes a first portion 50 and a second portion 52 of reduced diameter. The first portion 50 preferably tapers slightly as it extends into the adapter body 32 from a lower end 54 of the adapter body 32. The second portion 52 of the second generally cylindrical cavity 40 is shown to intersect the second portion 48 of the first generally cylindrical cavity 38. In a manner to be described further below, the stem insert 36 is partially disposed within the first portion 50 and extends into the second portion 52 where it engages the locking insert member 34.

Figure 10:
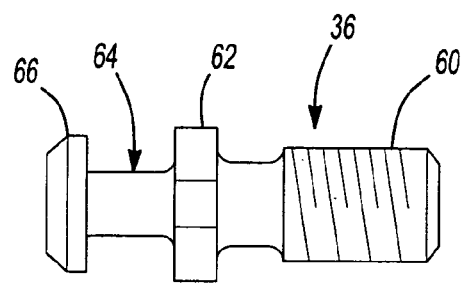
FIG. 10 is an enlarged view of the stem insert according to the present invention and shown in FIG. 6.
Figure 11:
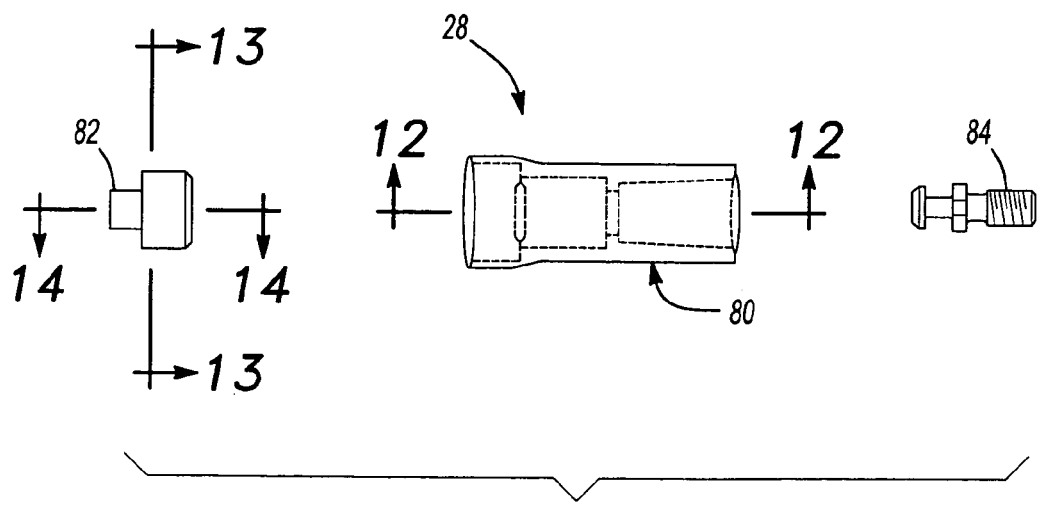
FIG. 11 is an exploded view similar to FIG. 6, illustrating a portion of the modular tibial component of FIG. 2.
Figure 12:
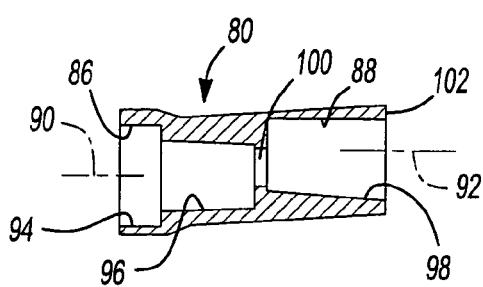
FIG. 12 is a cross-sectional view taken along the line 12—12 of FIG. 11.

With particular reference to FIG. 10, the stem insert member 36 is illustrated to include a lower portion 60 which is externally threaded for engaging an internally threaded aperture of the upwardly extending extension 42 of the stem 20. The stem insert member 36 further includes a central portion 62 having a hexagonal or other suitable cross-section which can be engaged by a tool (not shown) for rotating the stem insert member 36 into the stem 20. Further, the stem insert member 36 includes an upper end 64 including an enlarged diameter head 66 which extends into the second portion 52 of the second generally cylindrical cavity 40.

Figure 8:
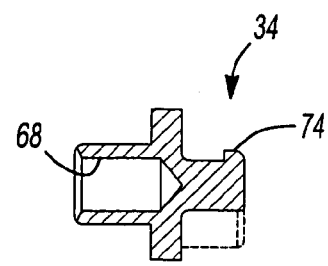
FIG. 8 is a cross-sectional view taken along the line 8—8 of FIG. 6.
Figure 9:
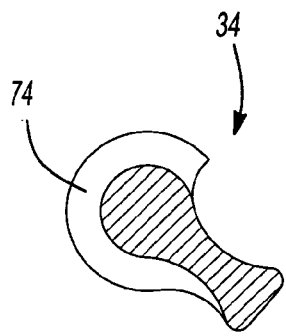
FIG. 9 is a cross-sectional view taken along the line 9—9 of FIG. 6.

With particular reference to the cross-sectional views of FIGS. 8 and 9, the locking insert member 34 will be further described. The locking insert member 34 includes an upper portion having an internally threaded aperture 68 and having a square, hexagonal or other suitable cross section that can be engaged by a tool (not shown). The internally threaded aperture 68 threadably receives a fastener 70 which extends through a central aperture 72 provided in the tray 22. The locking insert member 34 additionally includes a radially extending segment 74 for engaging the head 66 of the stem insert member 36.

Upon selection by the surgeon of the first adapter assembly 24, the stem insert member 36 is screwed into the stem 20. Next, the adapter body 32 is placed over the upwardly extending extension 42 of the stem 20 such that the upwardly extending portion 42 is received in a press fit within the first portion 50 of the first generally cylindrical aperture 40 and the upper end 64 of the stem insert member 36 extends into the reduced diameter second portion 52 of the second generally cylindrical cavity 40. At this point, the locking insert member 34 is inserted into the first generally cylindrical cavity 38 with the radially extending segment 74 opposite the side of the reduced diameter portion 48 which intersects the reduced diameter portion 52. Upon complete insertion, the locking insert member 34 is rotated approximately between 180° and 270° such that the radially extending portion 74 engages the enlarged head 66 of the stem insert member 36.

The adapter body 32 is rotated about the axis 27 to provide the offset in the desired direction. The first portion 46 of the first generally cylindrical cavity 38 is now press fit onto the downwardly extending extension 29 of the tray 22. The stem 20 is secured to the tray 22 by the threaded fastener 70 which extends through the aperture 72 and threadably engages the internally threaded aperture 68 of the locking insert member 34. Rotation of the threaded fastener 70 in a clockwise direction causes the locking insert member 34 to be drawn towards the tray 22 and a secure connection to be established between the tray 22 and the stem 20.

With reference now to FIGS. 2 and 11 through 14, the second adapter assembly 28 of the present invention will now be described. The second adapter assembly 28 is illustrated to generally include an adapter body 80, a locking insert member 82 and a stem insert member 84. The stem insert member 84 is identical to stem insert member 36 described above.

The adapter body 80 of the second adapter assembly 28 is shown to include a first generally cylindrical cavity 86 for receiving the downwardly extending extension 29 of the tray 22 and a second generally cylindrical cavity 88 for receiving the upwardly extending extension 42 of the stem 20. The first generally cylindrical cavity 86 includes a first central axis 90 and the second generally cylindrical cavity 88 includes a second generally cylindrical axis 92. In the embodiment illustrated, the first central axis 90 and the second central axis 92 are parallel to one another and spaced apart. Insofar as the second adapter assembly 80 provides a 2.5 mm offset, the first and second central axes 90 and 92 are spaced apart 2.5 mm.

The first generally cylindrical cavity 86 includes a first portion 94 for directly receiving the downwardly extending extension 29 of the tray 22 and a second reduced diameter portion 96 which receives the locking insert 82. As with the first adapter assembly 24, the first portion 94 preferably tapers slightly as it extends into the adapter body 80 from a top end. The second generally cylindrical cavity 88 similarly includes a first portion 98 and a second portion 100 of reduced diameter. The first portion 98 preferably tapers slightly as it extends into the adapter body 80 from a lower end 102 of the adapter body 80. The second portion 100 of the second generally cylindrical cavity 88 is shown to intersect the second portion 96 of the first generally cylindrical cavity 86.

Figure 14:
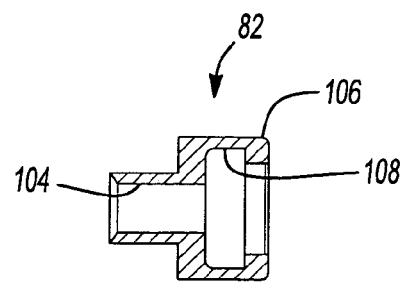
FIG. 14 is a cross-sectional view taken along the line 14—14 of FIG. 11.
Figure 13:
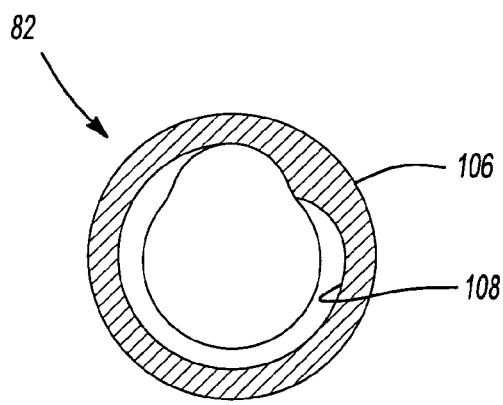
FIG. 13 is a cross-sectional view taken along the line 13—13 of FIG. 11.
Figure 16:
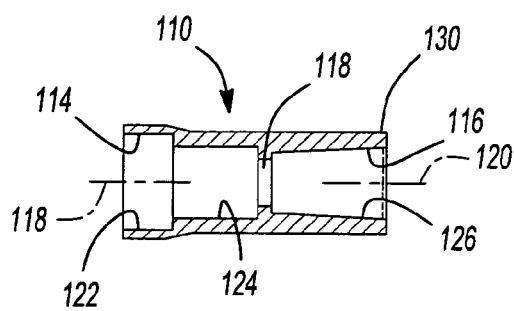
FIG. 16 is a cross-sectional view taken along the line 16—16 of FIG. 15.

With particular reference to the cross-sectional views of FIGS. 13 and 14, the locking insert member 82 will be further described. The locking insert member 82 includes an upper portion having an internally threaded aperture 104 and having a square, hexagonal or other suitable cross section that can be engaged by a tool. The internally threaded aperture 104 threadably receives the fastener 70 which extends through the central aperture 72 in the tray 22. The locking insert member 82 additionally includes a radially extending segment 106 defining a cavity 108 for engaging the head 66 of the stem insert member 36. The aperture 108 includes a non-cylindrical opening for receiving the head 66 of the stem insert member 36 and retaining the head 66 upon rotation in the manner discussed above with respect to the first adapter assembly 24.

With reference now to FIGS. 3 and 15 through 17, the third adapter assembly 30 of the present invention will now be described. The third adapter assembly 30 is illustrated to generally include an adapter body 110 and a locking insert member 112. The adapter body 110 of the third adapter assembly 30 is shown to include a first generally cylindrical cavity 114 for receiving the downwardly extending extension 29 of the tray 22 an a second generally cylindrical cavity 116 for receiving the upwardly extending extension 42 of the stem 20. The first generally cylindrical cavity includes a first central axis 118 and the second generally cylindrical cavity includes a second generally cylindrical axis 120. In the embodiment illustrated, the first central axis 118 and the second central axis 120 are coincident as the third adapter assembly 30 does not provide any offset.

The first generally cylindrical cavity 114 includes a first portion 122 for directly receiving the downwardly extending extension 29 of the tray 22 and a second reduced diameter portion 124 which receives the locking insert 112. The first portion 122 preferably tapers slightly as it extends into the adapter body 110 from an upper end. The second generally cylindrical cavity 116 similarly includes a first portion 126 and a second portion 128 of reduced diameter. The first portion 126 preferably tapers slightly as it extends into the adapter body 110 from a lower end 130 of the adapter body 110. The second portion 128 of the second generally cylindrical cavity 126 is shown to communicate with the second portion 124 of the first generally cylindrical cavity 114.

Figure 17:
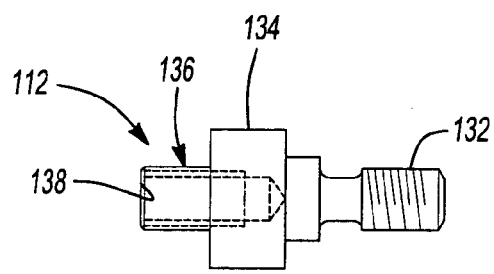
FIG. 17 is an enlarged view of the locking insert of FIG. 15.
Figure 15:
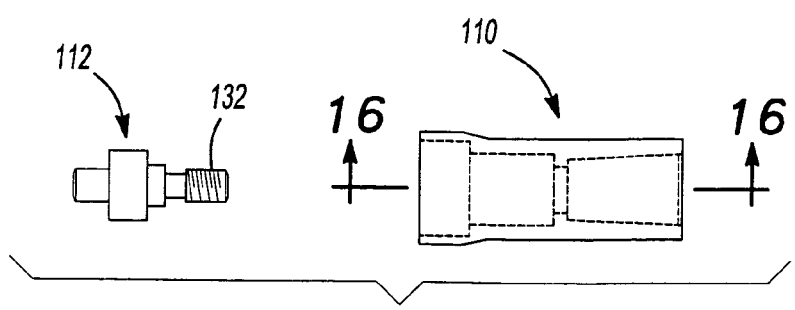
FIG. 15 is another exploded view similar to FIG. 6, illustrating a portion of the modular tibial component of FIG. 3.

With particular reference to FIG. 17, the locking insert member 112 is illustrated to include a lower portion 132 which is externally threaded for engaging the internally threaded aperture of the upwardly extending extension 42 of the stem 20. The locking insert member 112 further includes a central portion 134 and an upper portion 136. The upper portion has a square, hexagonal or other suitable cross section which can be engaged by a tool (not shown) for rotating the locking insert member 112 into the stem 20. The internally threaded aperture 138 threadably receives the fastener 70 which extends through the central aperture 72 provided in the tray 22.

Figure 18:
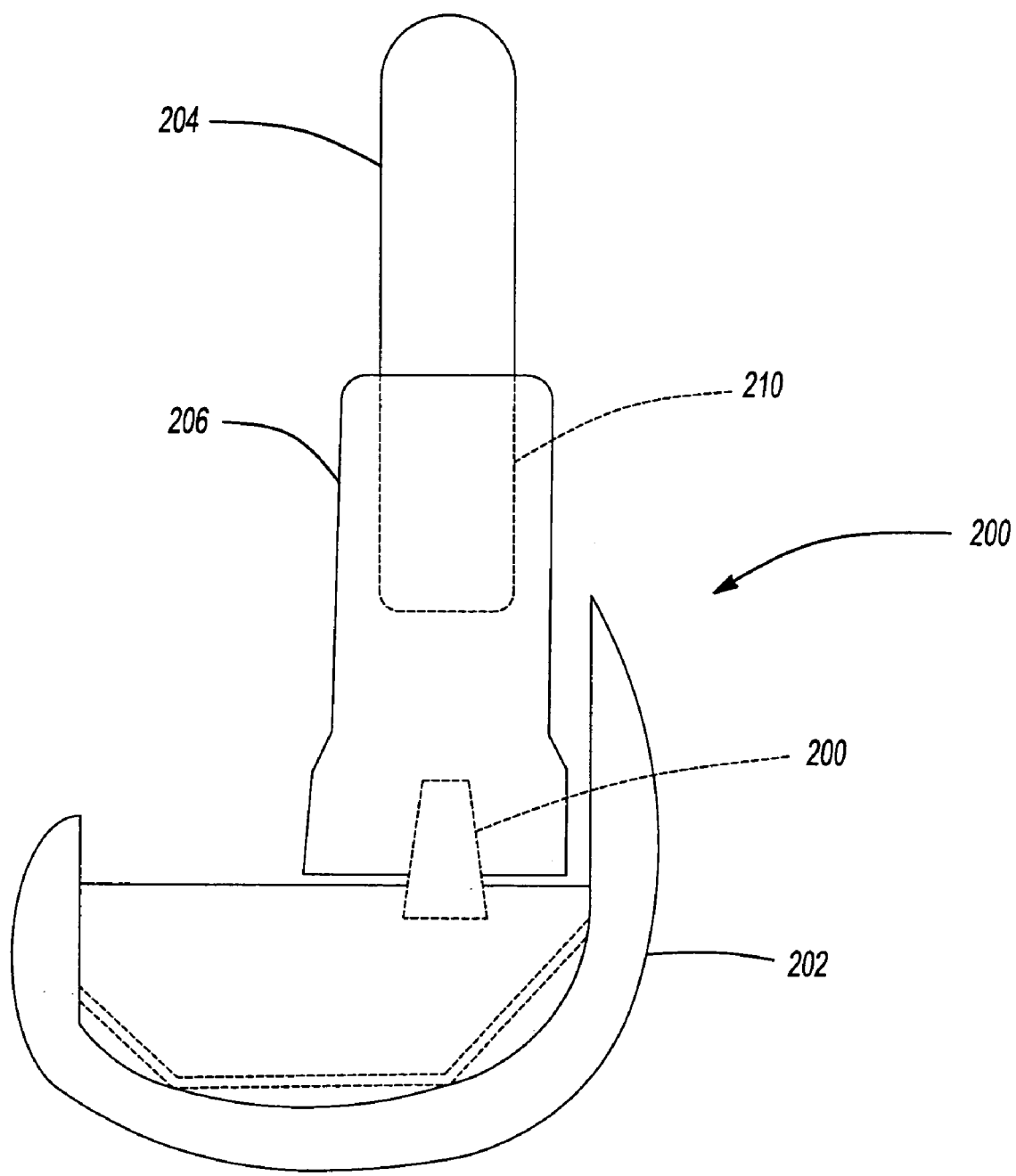
FIG. 18 is an illustration of a modular femoral component for a knee joint prosthesis according to the teachings of the present invention.

Turning to FIG. 18, a modular femoral component for a knee joint prosthesis of the present invention is generally identified at reference 200. The embodiment of FIG. 18 illustrates application of the teachings of the first preferred embodiment of the present invention adapted to a modular femoral component 200. The modular femoral component 200 includes an articulating member 202, a stem 204 and an adapter assembly 206. While not shown in great detail, it will be understood by those skilled in the art that the adapter assembly 206 is substantially identical to the first adapter assembly 24 described above. In this regard, the adapter assembly 206 connects the articulating member 202 and the stem 204 and provides an offset between an upwardly extending extension 208 of the articulating member and a downwardly extension 210 of the stem 204. The adapter assembly 206 will be understood to include an adapter body, locking insert member and stem insert member substantially identical to that described above with respect to the first adapter assembly 24. Alternatively, it will be understood that the adapter assembly of the modular femoral component 200 may be similar to either of the second and third adapter assemblies 28 and 30.

With reference to FIGS. 19, 20 and 21A through 21C, a tibial component for a knee joint prosthesis constructed in accordance with the teachings of a second preferred embodiment of the present invention is illustrated and generally identified at reference number 302. It will be understood that the knee joint prosthesis further includes a femoral component that cooperates with the tibial component 302. The particular construction of the femoral component is beyond the scope of the subject invention. One suitable femoral component is, however, shown in connection with the first preferred embodiment.

The tibial component 302 of the second preferred embodiment of the present invention will be understood to be modular in construction and generally include a stem 304, a tray 306, and an adapter assembly 308. In a manner which will be discussed more fully below, the adapter assembly 308 connects the tray 306 and the stem 304 so as to provide an offset to the stem 304 in the transverse plane. Explaining further, when the stem 304 is attached to the tray 306 through the adapter assembly 308, a central axis of the stem 304 is offset from a central axis of a downwardly extending extension 310 of the tray 306. In the embodiment illustrated, the adapter assembly 308 provides an offset of approximately 5 mm. As with the first preferred embodiment, the offset provided by the adapter assembly 308 preferably ranges from 0 mm to approximately 5 mm or more and can be in any direction in the transverse plane.

The adapter assembly 308 is illustrated to generally include an adapter body 312 and a locking member or element 314. The adapter body 312 of the adapter assembly 308 is shown to define a first cavity 316 for receiving the downwardly extending extension 310 of the tray 306 and a second cavity 318 for receiving and upwardly extending extension 320 of the stem 304. In the preferred embodiment, the first and second cavities 316 and 318 are generally cylindrical. The first cavity 316 includes a first central axis and the second cavity 318 includes a second cylindrical axis. Further, in the embodiment illustrated, the first central axis and the second central axis are parallel to one another and spaced apart. Insofar as the adapter assembly 308 provides a 5 mm offset, the first and second central axes are spaced apart 5 mm.

The first cavity 316 tapers slightly as it extends into the adapter body 312 from a top end 326 of the adapter body 312. The second cavity 318 similarly tapers slightly as it extends into the adapter body 312 from a lower end 322 of the adapter body 312. The adapter body 312 is illustrated to further define a laterally extending channel 324 which intersects both the first cavity 316 and the second cavity 318. In a manner to be described further below, the locking element 314 extends into the laterally extending channel 324 where it couples the tray 306 to the stem 304.

Figure 19:
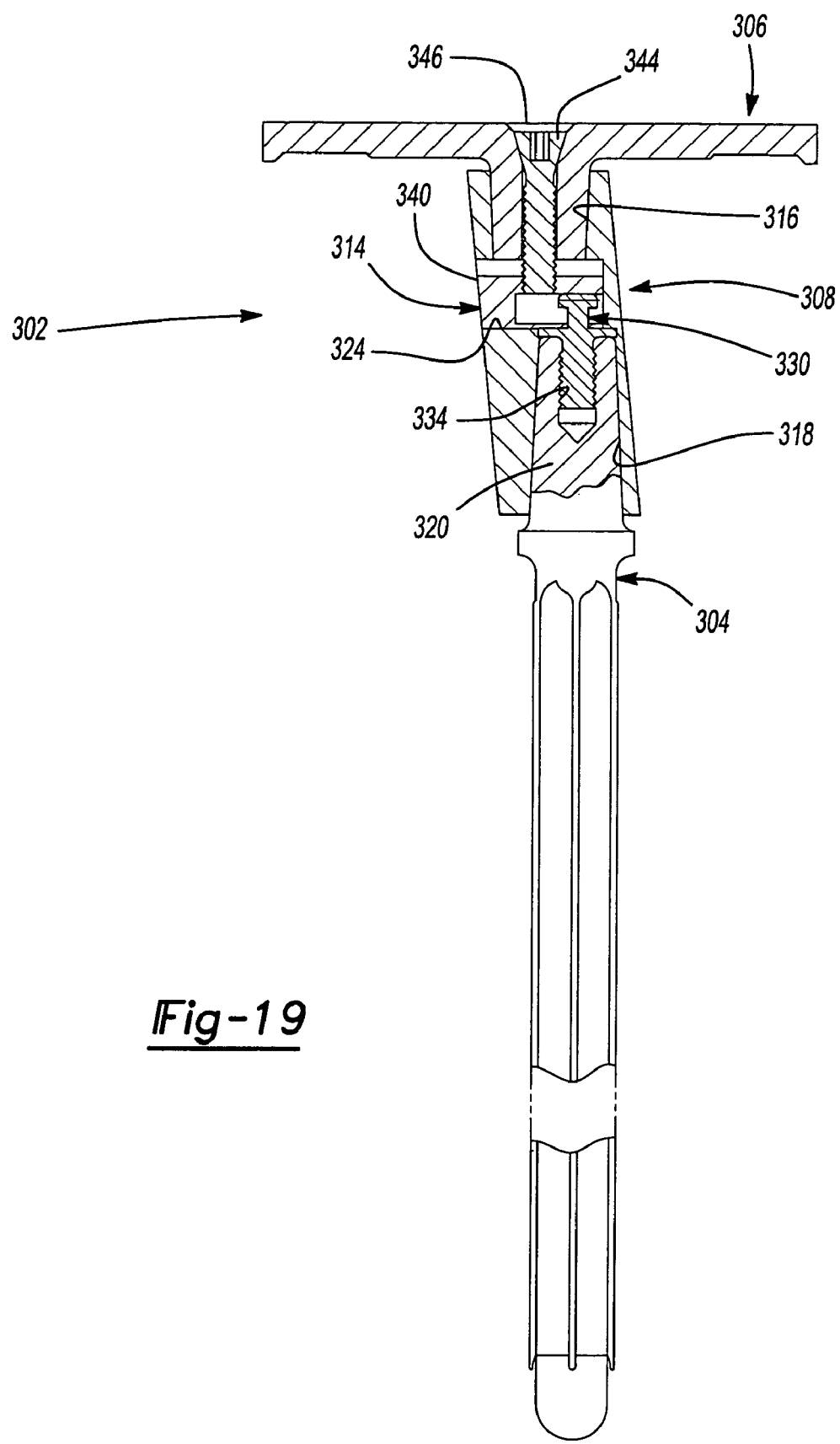
FIG. 19 is a front view illustration of a knee joint prosthesis constructed in accordance with the teachings of a second preferred embodiment of the present invention.
Figure 20:
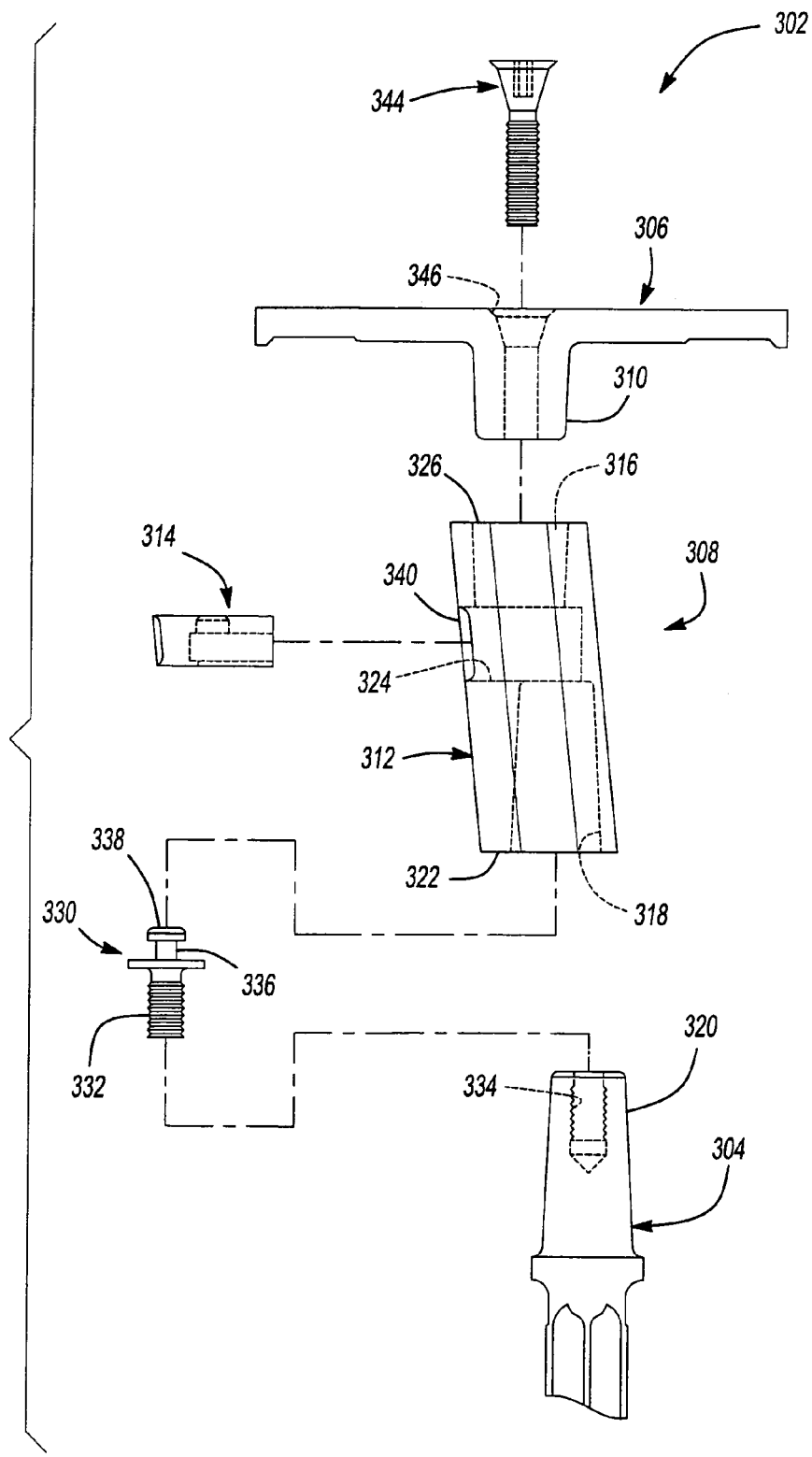
FIG. 20 is an exploded view of the knee joint prosthesis of FIG. 19.
Figure 21C:
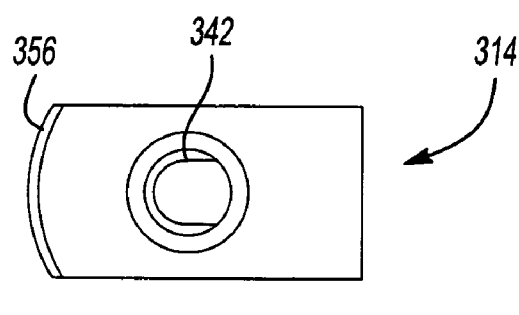
Figure 21C:
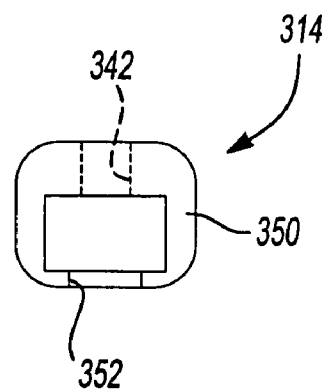
Figure 21C:
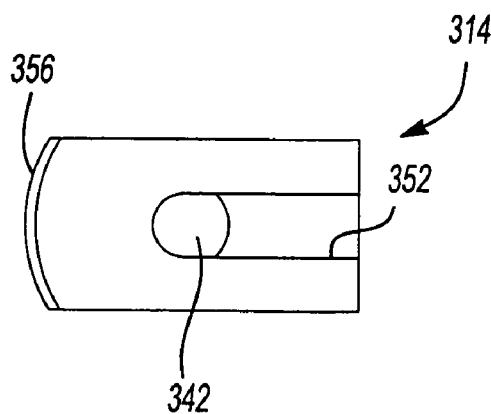

As shown in FIGS. 19 and 20, the stem 304 is illustrated to include an upper portion that cooperatively engages with the locking element 314. In the embodiment illustrated, the upper portion of the stem 304 includes a stem insert member. Alternatively, the upper portion of the stem 304 may be integrally formed to cooperate with the locking element 314.

The stem insert member 330 is illustrated to include a lower portion 332 which is externally threaded for engaging an internally threaded aperture 334 of the upwardly extending extension 320 of the stem 304. The stem insert member 330 further includes a central portion 336 having a hexagonal or other suitable cross-section which can be engaged by a tool (not shown) for rotating the stem insert member 330 into the stem 304. Further, the stem insert member 330 includes an upper end including an enlarged diameter head 338.

The locking element 314 is sized and configured to be inserted through an opening 340 in the sidewall of the adapter body 312 and into the channel 324 for coupling of the stem 304 and the tray 306. The locking element 314 includes an upper surface (see FIG. 19) having an internally threaded aperture 342. The internally threaded aperture 342 threadably receives a fastener 344 which extends through a central aperture 346 provided in the tray 306. The fastener 344 is aligned with the central longitudinal axis of the downwardly extending portion 310 of the tray 306.

The locking element 314 is illustrated to additionally include an open end 350 and a bottom surface having a slot 352. The slot 352 intersects the open end 350. The open end 350 receives the head 338 of the stem insert 330 as the locking element 314 is inserted through the opening 340. The slot 352 accommodates the reduced diameter, central portion 336 of the stem insert 330. The head 338 of the stem insert 330 has a diameter greater than a width of the slot 352 for coupling of the stem insert 330 with the locking element 314.

The locking element 314 further includes a closed end 356. The closed end 356 is preferably convexly curved. When the locking element 314 is completely inserted into the channel 324, the closed end 356 is flush with the sidewall of the adapter body 312.

In use, the stem insert member 330 is screwed into the stem 304. Next, the adapter body 312 is placed over the upwardly extending extension 320 of the stem 304 such that the upwardly extending portion 320 is received in a press fit within the second aperture 318 and the upper end of the stem insert member 330 extends into the laterally extending channel 324.

The first cavity 316 is now press fit onto the downwardly extending extension 310 of the tray 306 with the adapter body 312 oriented to provide the offset in the desired direction. At this point, the locking element 314 is inserted into the laterally extending channel 324 through the opening 340. Upon complete insertion, the locking element 314 engages the stem insert member 330. The tray 306 is secured to the adapter body 312 by the threaded fastener 344 which extends through the aperture 346 and threadably engages the internally threaded aperture 342 of the locking element 314.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A modular tibial component for a knee joint prosthesis, the modular tibial component comprising:

a tray having a support surface and a downwardly extending extension having a generally circular shape;

a stem having a main body portion and an upwardly extending extension;

an adapter body connecting the tray and the stem and establishing a relative offset between the downwardly extending extension of the tray and the upwardly extending extension of the stem, the adapter body including a first generally cylindrical cavity receiving the downwardly extending extension of the tray and a second generally cylindrical cavity intersecting the first generally cylindrical cavity and receiving the upwardly extending extension of the stem;

a locking arrangement for coupling the tray to the stem, the locking arrangement extending between the first and second generally cylindrical cavities, the locking arrangement including a first member removably engaging the tray and a second member removably engaging the stem, the first and second members rotatably coupled to one another within the adapter body; and wherein the first and second members are directly coupled to one another within the adapter body, wherein the first member threadably receives a fastener extending through the tray;

wherein the first member includes a radially extending portion engaging a reduced diameter portion of the second member.

2. A modular component for a joint prosthesis, the modular component comprising:

a joint component having a male extension;

a stem for engaging a canal of a bone, the stem having a main body portion and a male extension;

an adapter body for establishing a relative offset between the male extension of the joint component and the male extension of the stem, the adapter body including a first cavity receiving the male extension of the joint component and a second cavity receiving the male extension of the stem, the first cavity intersecting the second cavity;

a locking arrangement for coupling the joint component to the stem, the locking arrangement extending between the first and second cavities, the locking arrangement including a first member removably engaging the joint component and a second member removably engaging the stem, the first and second members rotatably coupled to one another within the adapter body; and wherein the first member threadably receives a fastener extending through the joint component.

3. A modular component for a joint prosthesis, the modular component comprising:

a joint component having a male extension;

a stem adapted to engage a canal of a bone, the stem having a main body portion and a male extension;

an adapter body for establishing a relative offset between the male extension of the joint component and the male extension of the stem, the adapter body including a first cavity receiving the male extension of the joint component and a second cavity receiving the male extension of the stem, the first cavity intersecting the second cavity; and a locking arrangement for coupling the joint component to the stem, the locking arrangement extending between the first and second cavities, the locking arrangement including a first member removably engaging the joint component and a second member removably engaging the stem, the first and second members being axially offset and rotatably coupled to one another within the adapter body.

4. The modular component of claim 3, wherein the first cavity includes a first reduced diameter portion and the second cavity includes a second reduced diameter portion, the first and second reduced diameter portions intersecting one another.

5. The modular component of claim 4, wherein the first reduced diameter portion of the first cavity receives the first member and the second reduced diameter portion of the second cavity partially receives the second member.

6. The modular component of claim 5, wherein the second member extends in the first reduced diameter portion of the first cavity engaging the first member therein.

7. The modular component of claim 6, wherein the first member includes a radially extending portion engaging a reduced diameter portion of the second member.

8. The modular component of claim 3, wherein the first member is rotatably coupled to the second member by rotation in the range of about 180°–270°.

* * * * *